(12) United States Patent
Babin et al.

(10) Patent No.: US 6,960,600 B2
(45) Date of Patent: Nov. 1, 2005

(54) AZOLE OR TRIAZOLE DERIVATIVES, METHOD FOR PREPARING THE SAME AND USE THEREOF AS ANTIFUNGAL MEDICAMENTS

(75) Inventors: Didier Babin, Montigny (FR); John Bernard Weston, Maisons Laffitte (FR)

(73) Assignee: Aventis Pharma S.A., Antony Cedex (FR)

( * ) Notice: Subject to any disclaimer, the term of this patent is extended or adjusted under 35 U.S.C. 154(b) by 24 days.

(21) Appl. No.: 10/476,942
(22) PCT Filed: May 2, 2002
(86) PCT No.: PCT/FR02/01519
§ 371 (c)(1), (2), (4) Date: Apr. 27, 2004
(87) PCT Pub. No.: WO02/090350
PCT Pub. Date: Nov. 14, 2002

(65) Prior Publication Data
US 2004/0192922 A1 Sep. 30, 2004

(30) Foreign Application Priority Data
May 4, 2001 (FR) ............................................. 01/05959

(51) Int. Cl.[7] .................... C07D 233/54; C07D 401/02; A61K 31/47; A61K 31/415
(52) U.S. Cl. ....................... 514/307; 514/383; 514/399; 546/139; 548/267.2; 548/335.5
(58) Field of Search ....................... 546/139; 548/336.5, 548/267.2; 514/307, 383, 399

(56) References Cited

FOREIGN PATENT DOCUMENTS

| EP | 0050298 | 4/1982 |
|---|---|---|
| EP | 0121753 | 10/1984 |
| WO | WO 0020413 | 4/2000 |
| WO | WO 0174808 | 10/2001 |

*Primary Examiner*—Zinna Northington Davis
(74) *Attorney, Agent, or Firm*—Balaram Gupta

(57) ABSTRACT

The invention concerns novel azole or triazole derivatives of formula (I), wherein: X, Ar¹, Ar³, A, R¹, R⁵, R⁶, R⁷ and B are such as defined in the description, their preparation method and their use as antifungal medicines.

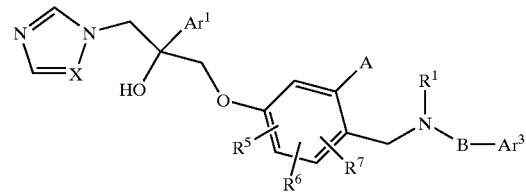

(I)

20 Claims, No Drawings

AZOLE OR TRIAZOLE DERIVATIVES, METHOD FOR PREPARING THE SAME AND USE THEREOF AS ANTIFUNGAL MEDICAMENTS

This application is a National Stage of International application No. PCT/FR02/01,519, filed May 2, 2002; which claims the benefit of priority of French Patent Application No. 01/05,959, filed May 4, 2001.

The present invention relates to new azole or triazole derivatives, their preparation process and their use as antifungal medicaments.

A number of compounds having an antifungal activity are known in the prior art. Azole derivatives as defined in the following Applications: EP 0 121 753 A (Hoechst A G), EP 0 050 298 A (Hoechst A G), U.S. Pat. No. 2,813,872 (J Schmutz), WO 00/20413 (Hoechst Marion Roussel) can in particular be mentioned. Nevertheless, a real need exists to make use of new antifungal compounds, the present strains being able to be or become resistant to the standard agents, in particular when the latter possess only a fungistatic activity. Moreover, the new antifungal compounds must be able to have improved solubility and must also be able to be absorbed more easily. Finally, the incidence of *Candida albicans* as an infectious agent, is increasing steadily, in particular vis-à-vis immunodeficient patients, for example as a result of HIV infection, and therefore requires new treatments.

The object of the present invention is to provide new compounds having an antifungal activity, in particular vis-à-vis *Candida* or *Aspergillus* strains.

A subject of the invention is the compounds of formula (I)

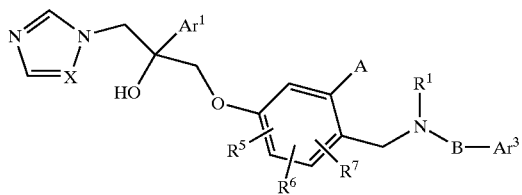

wherein

X is a nitrogen atom or a CH group, $Ar^1$ represents a carbocyclic or heterocyclic aryl, non-substituted or substituted by one or more $R^2$, $R^3$ or $R^4$ radicals A represents a hydrogen atom or represents a $CH_2$ group forming with $R^1$ a cyclic carbon-carbon bond, in order to obtain a ring with 6 members connected to the phenyl, $Ar^3$ represents a carbocyclic or heterocyclic aryl, non-substituted or substituted by one or more $R^8$, $R^9$ or $R^{10}$ radicals B represents a $(C_1-C_4)$-alkylene-CH=CH— radical or a $(C_1-C_4)$-alkylene-cyclopropylene radical, said cyclopropylene or —CH=CH— radicals being non-substituted or substituted by an $R^2$ and/or $R^3$ radical, $R^1$ represents a hydrogen atom, an —$SO_3H$ group, a $(C_1-C_6)$-alkyl radical, non-substituted or substituted by a radical as defined for $R^2$, or represents a $CH_2$ group forming with A a cyclic carbon-carbon bond, in order to obtain a ring with 6 members connected to the phenyl, $R^2$, $R^3$, $R^4$, $R^5$, $R^6$, $R^7$, $R^8$, $R^9$ or $R^{10}$, identical or different, represent fluorine, chlorine, bromine, cyano, mono- bi- or trihalogeno $(C_1-C_8)$alkyl, mono- bi- or trihalogeno $(C_1-C_8)$-alkyloxy, hydroxy, nitro, carboxyl, formyl, —$SO_3H$, —$OSO_3H$, $(R^{11}O)_2P(O)$—, $(R^{11}O)_2P(O)$—$O$—, amino, $(C_1-C_8)$-alkyl-amino, di$((C_1-C_8)$alkyl)amino, $(C_5-C_{14})$-aryl-$(C_1-C_6)$-alkylene-amino or $(C_5-C_{14})$-arylamino, $(C_1-C_8)$-alkyl, $(C_5-C_{14})$-aryl, a heterocycle optionally substituted by oxo, $(C_5-C_{14})$-aryl-$(C_1-C_6)$alkyl, amino-$(C_1-C_6)$-alkyl, $(C_1-C_8)$-alkylamino-$(C_1-C_6)$-alkyl, di-$((C_1-C_8)$alkyl)amino-$(C_1-C_6)$-alkyl, hydroxy-$(C_1-C_6)$alkyl, $(C_1-C_6)$-alkyloxy-$(C_1-C_6)$-alkyl, $(C_1-C_8)$-alkyloxy optionally interrupted by one or more oxygen atoms, $(C_5-C_{14})$-aryl-$(C_1-C_6)$-alkylenoxy, $(C_5-C_{14})$-aryloxy, hydroxy-$(C_1-C_6)$ alkylenoxy, $(C_1-C_6)$-alkyloxy-$(C_1-C_6)$-alkylenoxy, amino-$(C_1-C_6)$-alkylenoxy, $(C_1-C_6)$-alkylamino-$(C_1-C_6)$-alkylenoxy, di$((C_1-C_8)$-alkyl)amino-$(C_1-C_6)$-alkylenoxy, methylenedioxy, $(C_1-C_6)$-alkyloxycarbonyl, $(C_1-C_6)$-alkylcarbonyl, $(C_5-C_{14})$aryl-$(C_1-C_6)$-alkylenecarbonyl, $(C_5-C_{14})$-aryl-carbonyl, $(C_1-C_6)$-alkylaminocarbonyl, $(C_1-C_6)$-alkanoylamino, $(C_1-C_6)$-alkylsulfonylamino, $(C_5-C_{14})$-aryl-sulfonylamino, $(C_5-C_{14})$-aryl-$(C_1-C_6)$-alkylenesulfonylamino, $(C_1-C_6)$-alkylaminosulfonyl, $(C_5-C_{14})$-aryl-$(C_1-C_6)$-alkylenaminosulfonyl, $(C_1-C_6)$-alkylsulfonyl, $(C_5-C_{14})$-aryl-$(C_1-C_8)$-alkylenesulfonyl or $(C_5-C_{14})$-aryl-sulfonyl, said alkyl, aryl radicals or heterocycles being themselves non-substituted or substituted by one or more groups mentioned above.

$R^{11}$ represents hydrogen, $(C_1-C_{10})$-alkyl, $(C_6-C_{14})$-aryl or $(C_6-C_{14})$-aryl-$(C_1-C_6)$-alkyl, in all their possible stereoisomeric forms and their mixtures, as well as their physiologically acceptable addition salts and their prodrugs.

All the radicals which can be found several times in the compounds of formula (I), for example, the $R^2$ radical, are independent of one another and can be identical or different.

The alkyl radicals mentioned above can be linear, branched or cyclic, saturated or mono- or poly-unsaturated. This also applies when they carry a substituent or when they are included in groups such as for example alkoxy, alkoxycarbonyl or aralkyl.

By saturated $(C_1-C_8)$-alkyl is meant the methyl, ethyl, propyl, butyl, pentyl, hexyl, heptyl, octyl, nonyl radicals, the n-isomers of these radicals, isopropyl, isobutyl, isopentyl, neopentyl, isohexyl, 3-methyl-pentyl, 2,3,4-trimethylhexyl, sec-butyl, tert-butyl, tert-pentyl. Among the preferred radicals methyl, ethyl, n-propyl, isopropyl, n-butyl, isobutyl, and tert-butyl can be mentioned. By $(C_1-C_6)$-alkyl is meant the methyl, ethyl, propyl, butyl, pentyl, hexyl radicals and the n-isomers of these radicals.

By alkyloxy radical interrupted by one or more oxygen atoms, is preferably meant an O—$CH_2$—O—$(CH_2)_2$—O—$CH_3$-type radical.

The bivalent alkylene radicals corresponding to the monovalent radicals mentioned above are for example the methylene, ethylene, 1,3-propylene, 1,2-propylene (=1-methylethylene), 2,3-butylene (=1,2-dimethylethylene), 1,4-butylene, or 1,6-hexylene radicals.

The unsaturated alkyl radicals can contain one or more, for example one, two or three double and/or triple bonds. Of course, an unsaturated alkyl radical contains at least two carbon atoms. By unsaturated alkyl radical is meant therefore for example, the alkenyl radicals such as vinyl, 1-propenyl, allyl, butenyl, 3-methyl-2-butenyl or the alkynyl radicals such as ethynyl, 1-propynyl or propargyl.

By unsaturated bivalent alkylene radicals is meant the alkenylene and alkynylene radicals which can also be linear or branched. These are for example vinylene, propenylene, ethynylene or propynylene radicals.

The cycloalkyl radicals can be monocyclic, bicyclic or tricyclic. These are for example cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl radicals which can, if appropriate, be substituted for example by an alkyl containing from 1 to 4 carbon atoms. As substituted cycloalkyl radicals, 4-methylcyclo-hexyl, 2,3-dimethylcyclo-hexyl, dimethylcyclopropyl and dichlorocyclopropyl can be mentioned.

Unless otherwise indicated, the alkyl or cycloalkyl radicals can be non-substituted or substituted by one or more identical or different radicals chosen from $(C_1–C_6)$-alkyl, $(C_1–C_6)$-alkoxy, hydroxyl, halogen such as fluorine, chlorine and bromine, nitro, amino, trifluoromethyl, mono, —$OCF_3$, cyano, carboxyl, —$SO_3H$, —$OSO_3H$, $PO_3H_2$, $PO_3H_2$, $(C_1–C_4)$-alkoxycarbonyl, phenyl, phenoxy, benzyl and benzyloxy. Of course this also applies when the alkyl radical forms part of a group containing it, for example such as $(C_1–C_6)$-alkyloxycarbonyl, $(C_1–C_6)$-alkylcarbonyl or $(C_1–C_6)$-alkylaminocarbonyl.

By halogen is meant fluorine, chlorine, bromine or iodine.

By the term aryl is meant:
either the heterocyclic $(C_5–C_{14})$-aryl radicals (also generally known as $(C_5–C_{14})$-heteroaryl), in which the carbon atoms of the ring are replaced by a heteroatom such as nitrogen, oxygen or sulfur,
or the carbocyclic $(C_6–C_{14})$-aryl radicals.

Among the carbocyclic $(C_6–C_{14})$-aryl radicals, phenyl, naphthyl, biphenylyl, anthryl or fluorenyl and quite particularly 1-naphthyl, 2-naphthyl and phenyl can be mentioned.

Unless otherwise indicated, the aryl radicals, in particular phenyl, can be non-substituted or substituted by one or more identical or different radicals chosen from $(C_1–C_6)$-alkyl, $(C_1–C_6)$-alkoxy, hydroxyl, hydroxy$(C_1–C_6)$-alkyl, halogen such as fluorine, chlorine and bromine, nitro, amino, trifluoromethyl, —$OCF_3$, cyano, carboxyl, —$SO_3H$, —$OSO_3H$, $PO_3H_2$, $OPO_3H_2$, $(C_1–C_4)$-alkoxycarbonyl, phenyl, phenoxy, benzyl, benzyloxy and methylenedioxy.

In the case of monosubstituted phenyl, the substituent can be situated in position 2, 3 or 4, and preferably in position 3 or 4. Preferably, $Ar^3$ represents a phenyl substituted in position 4. In the case where the phenyl is di-substituted, the substituents can be in positions 2,3 or 2,4 or 2,5 or 2,6 or 3,4 or 3,5. Preferably, when $Ar^1$ represents a disubstituted phenyl, the two substituents are in positions 2,4. When this phenyl is tri-substituted the positions are as follows: 2,3,4 or 2,3,5 or 2,3,6 or 2,4,5 or 2,4,6 or 3,4,5. Similarly, the naphthyl radicals or other aryl radicals can be substituted in any position, for example the 1-naphthyl radical in positions 2-, 3-, 4-, 5-, 6-, 7-, and 8 and the 2-naphthyl radical in positions 1-, 3-, 4-, 5-, 6-, and 7.

The $(C_5–C_{14})$-aryl group can also represent a monocyclic or polycyclic aromatic system in which 1,2,3 or 4 carbon atoms of the ring are replaced by heteroatoms, in particular identical or different from the group constituted by nitrogen, oxygen and sulfur. Among the $(C_5–C_{14})$-heterocyclic aryl (also generally known as $(C_5–C_{14})$-heteroaryl) groups, 2-pyridyl pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl groups, or also benzo-condensed, cyclopenta-, cyclohexa-, or cyclohepta-condensed derivatives of these radicals can be mentioned.

The heterocyclic system can be substituted by the same substituents mentioned above for the carbocyclic system.

Of course, the above description concerning the aryl groups also applies when aryl is a radical included in a group such as aryl-alkyl. As preferred examples of aryl-alkyl groups, benzyl, 1-phenylethyl or 2-phenylehyl can be mentioned.

By heterocycle, is preferably meant a non-aromatic radical with 5 members, optionally containing one or two double bonds and one or more nitrogen or oxygen atoms substituted or non-substituted by the same substituents mentioned above for the carbocyclic system as well as the oxo radical. The invention thus comprises the following heterocycles:

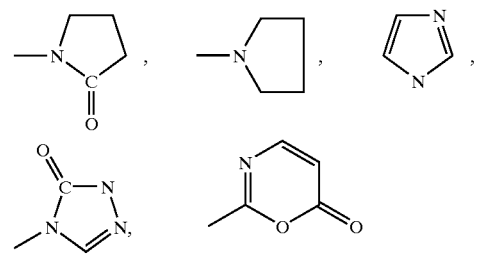

These heterocycles being able to be substituted. They can then be the following radicals:

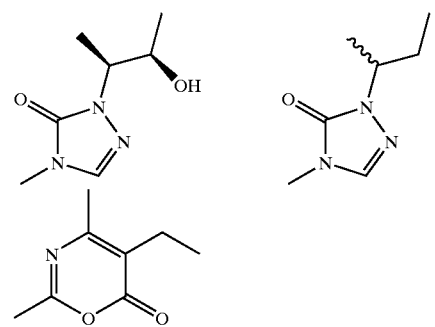

The optically active carbon atoms contained in the compounds of formula (I) can independently of one another have the R configuration or S configuration.

The compounds of formula (I) can be in the form of pure enantiomers or pure diastereoisomers or in the form of a mixture of enantiomers, for example in the form of racemates or mixtures of diastereoisomers.

A subject of the present invention is therefore the pure enantiomers, mixtures of these enantiomers, pure diastereoisomers and mixtures of these diastereoisomers.

The invention comprises the mixtures of two or more than two stereoisomers of formula (I) and all the ratios of these stereoisomers in said mixtures.

The compounds of formula (I) can, if appropriate, be present in the form of E isomers or Z isomers. A subject of the invention is therefore the pure E isomers, pure Z isomers and E/Z mixtures according to any ratio. When the compounds of formula (I) contain a cyclopropane, these compounds of formula (I) can be present in the form of cis or trans isomers. A subject of the invention is therefore the pure cis isomers, pure trans isomers and cis/trans mixtures according to any ratio.

The invention also comprises all the tautomeric forms of the compounds of formula (I). The diastereoisomers, including the E/Z (or cis/trans) isomers can be separated into individual isomers, for example by chromatography. The racemates can be separated into two enantiomers by standard methods such as chiral phase chromatography or by resolution methods.

The physiologically acceptable salts of the compounds of formula (I) are in particular pharmaceutically useful or non-toxic or physiologically useful salts.

When the compounds of formula (I) contain an acid group such as carboxylic acid, these are for example alkali metal or alkaline-earth salts such as sodium, potassium, magnesium, calcium salts, and also salts formed with physiologically acceptable quaternary ammonium ions and the addition salts with acids such as ammonia and physiologically acceptable organic amines such as for example triethylamine, ethanolamine or tris-(2-hydroxyethyl)amine.

When the compounds of formula (I) contain a basic group, they can form an addition salt with acids, for example with inorganic acids such as hydrochloric, sulfuric, phosphoric acid or with the organic carboxylic acids such as acetic, trifluoroacetic, citric, benzoic, maleic, fumaric, tartaric, methanesulfonic or para toluene sulfonic acid.

The compounds of formula (I) which comprise a basic group and an acid group, such as for example guanidino and carboxylic, can be present in the form of zwitterions (betaines), which are also included in the present invention.

When the compounds of Formula (I) contain a charged ammonium group, the counter anion (Q$^-$) is preferably a monovalent anion or a polyvalent anion equivalent of a physiologically acceptable and in particular pharmaceutically acceptable non-toxic organic or inorganic acid, for example the anion or an anion equivalent of one of the acids mentioned above, which is useful for the formation of the addition salts. The counter anion, Q$^-$, can be for example one of the anions (or anion equivalents) of a group chosen from chlorine, sulfate, phosphate, acetate, trifluoroacetate, citrate, benzoate, maleate, fumarate, tartrate, methanesulfonate and para-toluenesulfonate.

The salts of the compounds of formula (I) can be obtained by ordinary methods known to a person skilled in the art, for example by combining a compound of formula (I) with an organic or inorganic acid or a base in a solvent or a dispersant or from another salt by cation or anion exchange.

The invention also includes all the salts of the compounds of formula (I) which, because of their low physiological acceptability, cannot be used directly as a medicament, but can be used as intermediate products for use in later chemical modifications to the compounds of formula (I) or as starting products for the preparation of physiologically acceptable salts.

The present invention also includes all the solvates of the compounds of formula (I) for examples hydrates, solvates formed with alcohols, and all the derivatives of the compounds of formula (I), for example esters, prodrugs and other physiologically acceptable derivatives, as well as the metabolites of the compounds of formula (I).

A subject of the invention is also the prodrugs of the compounds of formula (I) which can be converted to compounds of formula (I) in vivo under physiological conditions. The prodrugs of the compounds of formula (I), namely the derivatives of the compounds of formula (I) chemically modified in order to obtain properties improved in the desired manner, are known to a person skilled in the art.

In order to have more information on the type of prodrug envisaged in the present invention, the following works can be mentioned: Fleicher et al., Advanced Drug Delivery Review 19 (1996) 115–130; Design of prodrugs, H. Bundgaard, Ed., Elsevier, 1985; H. Bundgaard, Drugs of the Future 16 (1991) 443; Saulnier et al. Bioorg. Med. Chem. Lett. 4 (1994) 1985; and Safadi et al. Pharmaceutical Res. 10 (1993) 1350. Among the appropriate prodrugs of the compounds of formula (I) the following can preferably be mentioned:

the prodrugs in the form of esters of the carboxylic, sulfonic or phosphonic groups, when, for example, $Ar^3$ is substituted respectively by a —$CO_2H$, —$SO_3H$ or —$PO_3H$ group.

the prodrugs in the form of acyl and carbamate for the groups containing an acylable nitrogen such as the amino or guanidine groups.

The prodrugs in the form of quaternary derivatives of N such as substituted benzyl.

In the prodrugs which are acylated, or in carbamate form, once or more times, for example twice, a hydrogen atom situated on the nitrogen atom is replaced by an acyl or carbamate group. Among the preferred acyl or carbamate groups, the $R_{12}CO$—, $R_{13}OCO$— groups can be mentioned, in which $R_{12}$ is a hydrogen or a ($C_1$–$C_{18}$)-alkyl, ($C_3$–$C_{14}$)-cycloalkyl, ($C_3$–$C_{14}$)-cycloalkyl-($C_1$–$C_8$)-alkyl, ($C_5$–$C_{14}$)-aryl radical, in which 1 to 5 carbon atoms can be replaced by heteroatoms such as N, O, S or ($C_5$–$C_{14}$)-aryl-($C_1$–$C_8$) alkyl, in which 1 to 5 carbon atoms in the aryl part can be replaced by heteroatoms such as N, O, S and $R_{13}$ with the same values as $R_{12}$ with the exception of hydrogen.

Of course, $Ar^1$, $Ar^3$, $R^1$, $R^2$, $R^3$, $R^4$, $R^5$, $R^6$, $R^7$, $R^8$, $R^9$, $R^{10}$, $R^{11}$, $R^{12}$ and $R^{13}$ can adopt the above definitions independently of one other.

Among the definitions relating to formula (I), the following preferred moieties can be mentioned:

$Ar^1$ and $Ar^3$ are preferably phenyls, $Ar^1$ represents a phenyl group and $Ar^3$ represents a heterocycle, A is preferably a hydrogen or represents a CH$_2$ group linked to R$^1$ by a cyclic carbon-carbon bond in order to form, with the connected phenyl, a tetrahydroisoquinoline, B is preferably a —CH$_2$—CH=CH— or —CH$_2$-(cyclopropyl)-group said groups being non-substituted or substituted by one or more halogens or (C$_1$–C$_4$)-alkyl, R$^1$ is preferably a hydrogen atom or a methyl or ethyl group, non-substituted or substituted by a fluorine, OH, NH$_2$, (C$_1$–C$_8$)-alkyloxy, (C$_1$–C$_8$)-alkylamino, pyrrolidino, 2-oxopyrrolidino, or di-(C$_1$–C$_8$)-alkylamino group, or represents a CH$_2$ group linked to A by a cyclic carbon-carbon bond in order to form, with the connected phenyl, a tetrahydroisoquinoline, R$^2$ and R$^3$ are preferably halogen atoms R$^4$ is preferably a hydrogen atom R$^6$ is preferably a hydrogen atom R$^5$ and R$^7$ preferably represent hydrogen R$^8$, R$^9$ and R$^{10}$ preferably represent hydrogen, halogen, —CF$_3$CN, —OCF$_3$, —OH, —SO$_3$H, —P(O)(OH)$_2$, carboxy, —OSO$_3$H, —OPO$_3$H, —NH$_2$, (C$_1$–C$_6$)-alkyl, a non-aromatic saturated or unsaturated heterocyclic radical, amino-(C$_1$–C$_6$)-alkyl, hydroxy-(C$_1$–C$_6$)-alkyl, (C$_1$–C$_6$)-alkyloxy, (C$_1$–C$_6$)-alkylamino-(C$_1$–C$_6$)-alkyloxy, (C$_1$–C$_6$)-alkyloxycarbonyl, (C$_1$–C$_6$)-alkylcarbonyl, (C$_1$–C$_6$)-alkylaminocarbonyl, (C$_1$–C$_6$)-alkylamino, di-(C$_1$–C$_6$)-alkylamino or di-(C$_1$–C$_6$)-alkylamino-(C$_1$–C$_6$)-alkyloxy, said alkyl radicals being non-substituted or substituted by halogen, OH, SO$_3$H, P(O)(OH)$_2$, carboxy, —OSO$_3$H, —OPO$_3$H$_2$, —NH$_2$, phenyl, (C$_1$–C$_6$)-alkyloxy, (C$_1$–C$_6$)-alkylamino or di-(C$_1$–C$_6$)-alkylamino.

A more particular subject of the invention is the compounds of formula (I) as defined above in which B is a —CH$_2$—CH=CH— or —CH$_2$-(cyclopropyl)-group, said groups being non-substituted or substituted by one or more halogens or (C$_1$–C$_4$)-alkyl, Ar$^1$ represents a phenyl disubstituted by R$^2$ and R$^3$, as well as their physiologically acceptable addition salts.

A more particular subject of the invention is the compounds of formula (I) as defined above corresponding to the formula:

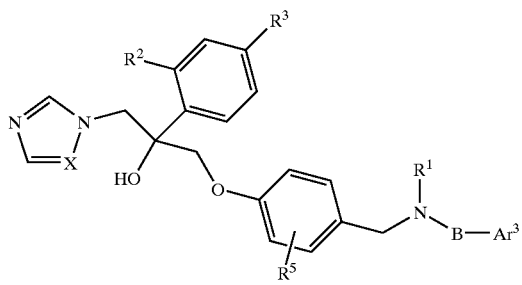

in which, B, X, Ar$^3$, R$^5$ and R$^1$ are as defined above, R$^2$ and R$^3$ represent a chlorine or fluorine atom as well as their physiologically acceptable addition salts.

A more particular subject of the invention is the compounds of formula (I) as defined above corresponding to formula (Ib):

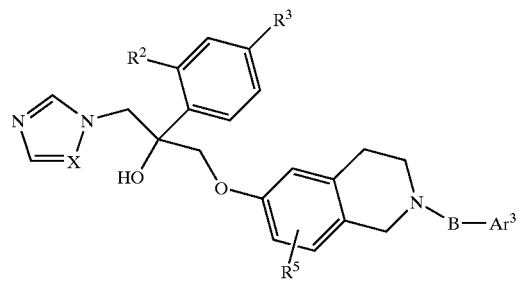

in which, B, X, Ar$^3$, R$^5$ and R$^1$ are as defined above, R$^2$ and R$^3$ represent a chlorine or fluorine atom, as well as their physiologically acceptable addition salts.

A more particular subject of the invention is the compounds of formula (I), (IA) or (IB) as defined above in which R$_2$ and R$_3$ are fluorine or chlorine atoms, X represents CH or NH, and Ar$^3$ represents a phenyl group, non-substituted or substituted by R$^8$ as defined previously, as well as their physiologically acceptable addition salts.

A quite particular subject of the invention is the compounds of formula (I) or (IA) as defined previously, in which R$^1$ is a hydrogen atom or a methyl or ethyl group, non-substituted or substituted by an F, OH, NH$_2$, (C$_1$–C$_6$)-alkyloxy, (C$_1$–C$_6$)-alkylamino, pyrrolidino, 2-oxopyrrolidino, or di-(C$_1$–C$_6$)-alkylamino group, as well as their physiologically acceptable addition salts.

A quite particular subject of the invention is the compounds of formula (I), (IA) or (IB) as defined previously in which Ar$^3$ is a phenyl, non-substituted or substituted by R$^8$ representing a —Cl, —F, CN, —CF$_3$, —OCF$_3$, —OH, —NH$_2$, (C$_1$–C$_6$)-alkyloxy, (C$_1$–C$_6$)-alkylamino, or di-(C$_1$–C$_6$)-alkylamino radical or a heterocycle chosen from:

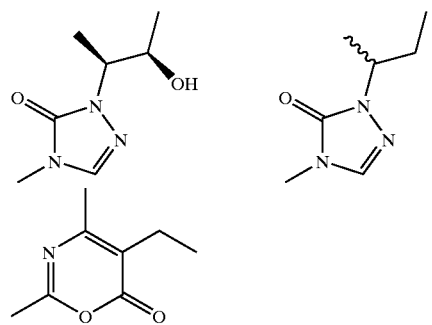

A quite particular subject of the invention is the following compounds:
alpha-[[[2-[3-(4-chlorophenyl)-2(E)-propenyl]-1,2,3,4-tetrahydro-6-isoquinolinyl]oxy]methyl]-alpha-(2,4-dichlorophenyl)-1H-imidazol-1-ethanol;
alpha-(2,4-dichlorophenyl)-alpha-[[4-[[[methyl(3-phenyl-2(E)-propenyl)]amino]methyl]phenoxy]methyl]-1H-imidazol-1-ethanol;
alpha-(2,4-difluorophenyl)-alpha-[[4-[[methyl(3-phenyl-2(E)-propenyl)amino]methyl]phenoxy]methyl]-1H-1,2,4-triazol-1-ethanol;
alpha-[[[2-[3-(4-chlorophenyl)-2(E)-propenyl]-1,2,3,4-tetrahydro-6-isoquinolinyl]oxy]methyl]-alpha-(2,4-difluorophenyl)-1H-1,2,4-triazol-1-ethanol; and alpha-(2,4-difluorophenyl)-alpha-[[4-[[(2-aminoethyl)[3-(4-chlorophenyl)-2(E)-propenyl]amino]methyl]phenoxy]methyl]-1H-imidazol-1-ethanol.

A subject of the invention is also a process for the preparation of the compounds of formula (I) characterized in that a compound of formula (II)

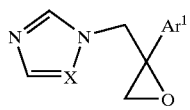

(II)

in which X and Ar¹ are as defined previously is subjected to the action of a compound of formula (IIIa) or (IIIb)

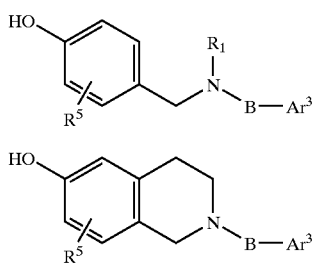

(IIIa)

(IIIb)

in which $R^1$, $R^5$, B and $Ar^3$ retain their previous meaning, in a basic medium, in order to obtain the corresponding compound of formula (IA) or (IB).

This reaction is preferably carried out in the presence of $K_2CO_3$ in DMF, and optionally with an 18-C-6 type crown ether.

As a variant of the process, the compound of formula (II) is reacted with an aryl of formula (III') HO—$C_6H_4$—CHO in the presence of a base, the phenyl being non-substituted or substituted by $R^5$ in order to obtain a compound of formula (IIa)

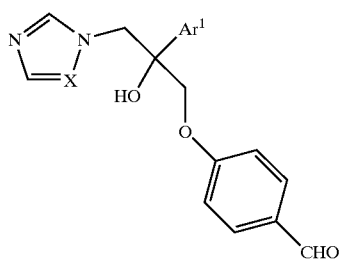

(IIa)

which is reacted with an amine of formula $R^1$—$NH_2$, $R^1$ being as defined previously, the reactive functions of which are optionally protected, followed by a reduction reaction in the presence of a reducing agent such as $NaBH_3CN$ or $BH_3$.pyridine, in order to obtain a compound of formula (IIb)

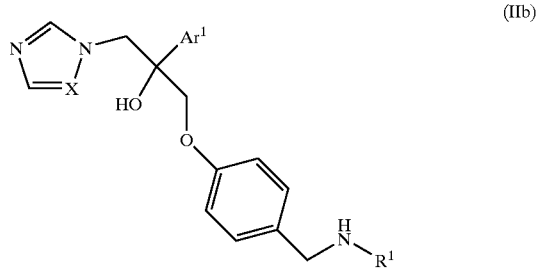

(IIb)

which is reacted
either with a derivative of formula

OHC—CH=CH—$C_6H_4$—$R^8$ or OHC-(cyclopropyl)-$C_6H_4$—$R^8$ followed by a reduction reaction in the presence of a reducing agent such as $NaBH_3CN$
or with a compound of formula:

AcO—$CH_2$—CH=CH—Ph—$R^8$ in the presence of a palladium derivative in order to obtain the following compounds of formula (IAA) or (IAB):

(IAA)

(IAB)

The first reducing amination reaction involving aldehyde (IIa) is carried out preferably in the presence of a reagent such as $NaBH_3CN$ in methanol or pyridin.$BH_3$. The second reducing amination reaction involving amine (IIc) with a trans-cinnamaldehyde derivative, is also carried out preferably in the presence of $NaBH_3CN$ in methanol. The reaction involving the amine (IIc) with an allyl acetate is carried out in the presence of a palladium derivative, for example in an acetonitrile/water medium (tppts/Pd(OAc)₂).

The starting compounds of formula (II) or (III) can be prepared according to processes described in the literature or are also accessible by analogy. The preparation of the compounds of formula (II) is carried out according to the following diagram:

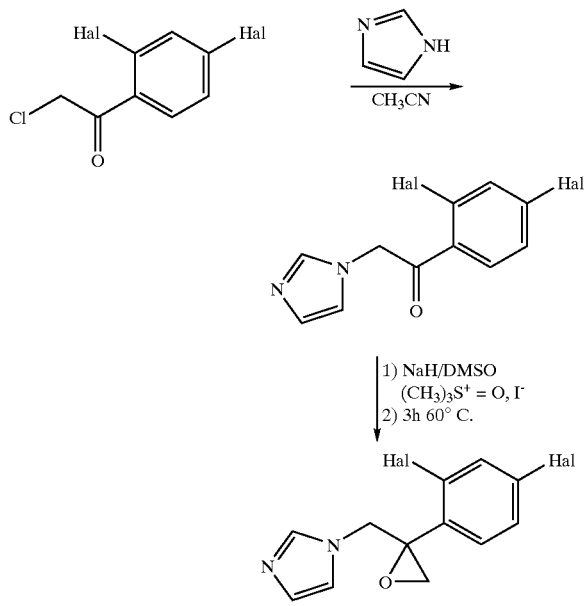

Certain compounds of formula (III) (R¹=Me) are easily accessible. They can be prepared as indicated in the diagram below or in the experimental part.

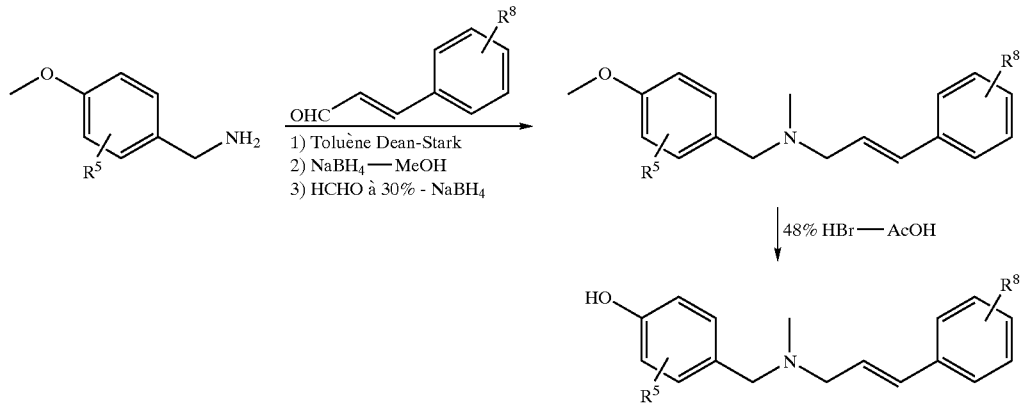

The compounds of formula III such as (E)-2-[3-phenyl)-2-propenyl]1,2,3,4-tetrahydro-6-isoquinolinol or its derivatives (phenyl substituted by R⁸) are prepared according to the method described in WO 00/20413.

It being understood that the present invention is not restricted to these syntheses or to these starting products. There is no major difficulty for a person skilled in the art to provide modifications to the syntheses described in our Application for the preparation of other compounds of formula (I) according to the invention.

The compounds of formula (I) are compounds having a pharmacological activity and can thus be used as medicaments, in particular as antifungals.

A subject of the present invention is therefore the compounds of formula (I) and/or their physiologically acceptable salts and/or their prodrugs as medicaments.

The compounds of formula (I) as well as their physiologically acceptable salts and their prodrugs can be administered to animals, preferably to mammals and in particular to human beings as therapeutic or prophylactic medicaments.

The compounds of formula (I) have useful antifungal properties. They are in particular active on *Candida albicans* and other *Candida* such as *Candida glabrata, krusei, tropicalis, pseudotropicalis* and *parapsilosis,* on *Aspergillus, Aspergillus flavus, Aspergillus niger, Cryptococcus neoformans, Microsporum canis, Trichophyton rubrun, Trichophyton mentagrophyte.*

The compounds of formula (I) can be used as medicaments in humans or animals, in particular to combat digestive, urinary, vaginal or cutaneous candidoses, cryptococcoses, for example neuromeningeal, pulmonary or cutaneous cryptococcoses, bronchopulmonary and pulmonary aspergilloses and invasive aspergilloses in immunodeficient individuals.

The compounds according to the invention can also be used in the prevention of mycosic diseases in individuals with congenital or acquired immunodeficiency.

The compounds of the invention are not limited to a pharmaceutical use. They can be also used as fungicides in fields other than that of pharmaceuticals.

A subject of the invention is therefore as antifungal medicaments, the compounds of formula (I).

The compounds according to the invention can be administered as they are or in a mixture with one or more other compounds of formula (I) or also in the form of a pharmaceutical preparation (pharmaceutical composition) which allows enteral or parenteral administration and which contains as active compound an effective dose of at least one compound of formula (I) and/or its physiologically acceptable salts and/or its prodrugs as well as standard and pharmaceutically inert supports and/or additives.

The pharmaceutical compositions according to the invention allow enteral or parenteral administration, containing as active compound an effective dose of at least one compound of formula (I) and/or its physiologically acceptable salts and/or its prodrugs as well as one or more pharmaceutically inert supports, and/or one or more usual additives.

A subject of the invention is therefore the pharmaceutical compositions containing a compound of formula (I) as defined previously as well as a vehicle.

The medicaments can be administered orally, for example in the form of pills, tablets, coated tablets, flakes, granules, gelatin capsules and soft capsules, solutions, syrups, emulsions, suspensions or aerosol mixtures.

The administration can however be carried out by rectal route, for example in the form of suppositories, by parenteral route, for example in the form of injectable solutions or infusions, microcapsules or implants, by percutaneous route, for example in the form of ointments, solutions, pigments or coloring agents, by transdermal route in the form of patches or by other routes such as in the form of nasal aerosols or sprays.

The pharmaceutical compositions according to the invention are prepared according to methods known per se, pharmaceutically inert organic or inorganic supports being added to the compounds of formula (I) and/or their physiologically acceptable salts and/or their prodrugs.

For the production of pills, tablets, coated tablets and hard gelatin capsules, it is possible to use for example, lactose, cornstarch or its derivatives, talc, stearic acid or its salts, etc. Suitable supports for soft gelatin capsules or suppositories are for example fats, waxes, semi-solid or liquid polyols, natural or modified oils etc. Appropriate supports for the preparation of solutions, for example injectable solutions, emulsions or syrups are for example water, alcohols, glycerol, polyols, sucrose, inverted sugars, glucose, vegetable oils, etc. Suitable supports for microcapsules or implants are for example glyoxylic acid and lactic acid copolymers. The pharmaceutical preparations normally contain from 0.5% to 90% by weight of compounds of formula (I) and/or their physiologically acceptable salts.

In addition to the active ingredients and supports, the pharmaceutical preparations can contain additives such as for example diluents, disintegrating agents, binders, lubricants, wetting agents, stabilizers, emulsifiers, preservatives, sweeteners, coloring agents, flavoring agents, thickeners, buffering agents, and also solvents or solubilizers or agents for obtaining a delayed effect and also salts for modifying the osmotic pressure, coating agents or antioxidants.

They can also contain two or more compounds of formula (I) and/or their physiologically acceptable salts and/or their prodrugs. Moreover, in more than at least one or more compounds of formula (I) and/or their physiologically acceptable salts and/or their prodrugs, they can contain at least one or more other useful active ingredients as therapeutics or prophylactics.

The pharmaceutical preparations (pharmaceutical compositions) normally contain from 0.2 to 500 mg, and preferably from 1 to 200 mg of the compound of formula (I) and/or their physiologically acceptable salts and/or their prodrugs.

A more particular subject of the present invention is therefore a compound of formula (I) and/or its physiologically acceptable salts and/or its prodrugs as defined above as a medicament having an antifungal activity.

A subject of the present invention is also the use of the compounds of formula (I) and/or their physiologically acceptable salts and/or their prodrugs as defined above for the preparation of antifungal medicaments.

When the compounds of formula (I) are used, the doses can vary within broad limits and must be fixed as a function of the person to be treated. This depends for example on the compound used or the nature and severity of the disease to be treated and whether serious or chronic conditions prevail or a prophylactic treatment is being implemented.

In the case of administration by oral route, the daily dose generally varies from 0.01 to 100 mg/kg and preferably from 0.1 to 50 mg/kg, in particular from 0.1 to 5 mg/kg.

In the case of administration by intravenous route, the daily dose varies approximately from 0.01 to 100 mg/kg and preferably from 0.05 to 10 mg/kg.

The daily dose can be divided, in particular in the case of the administration of a large quantity of active ingredient, into several, for example 2, 3 or 4 parts. If appropriate, as a function of individual behavior, it can be necessary to administer the different doses in increasing or decreasing manner.

The compounds of formula (I) and their salts can also be used as intermediates for the preparation of other compounds, in particular other active ingredients, which are accessible from the compounds of formula (I), for example by modification or introduction of radicals or functional groups.

A subject of the invention is also, as intermediate compounds, the compounds of formulae (IIa) and (IIb) as defined above.

EXAMPLES

The products were characterized by mass spectroscopy (MS), infrared (IR) and/or NMR spectroscopy. The compounds were purified by normal-phase (in particular in the presence of a $CH_2Cl_2$/MeOH mixture) or reversed-phase chromatography (in the presence of acetic or trifluoroacetic acid). The compounds of formula (I) are purified using an eluent which contains for example trifluoroacetic acid, and which are then dried or in which, during the last synthesis stage, for example trifluoroacetic acid was used in order to eliminate a tert-butyl protective group, sometimes contain, depending on the manner in which the product was dried, the acid originating from the eluent or the last synthesis stage and are therefore found partially or completely in the form of the salt of the acid used, for example in the form of an acetic or trifluoroacetic acid salt. They can also be more or less hydrated.

Abbreviations/Chemical Names Optionally Used:

AcOEt: ethyl acetate; DMF: dimethylformamide; HOBt: 1-hydroxybenzotriazole hydrate, MeOH: methanol; TEA: triethylamine; TFA: trifluoroacetic acid; THF: tetrahydrofuran; MCPBA: meta-chloroperoxybenzoic acid; DBU: 1,8-diazabicyclo[5.4.0]undec-7-ene; PTSA: paratoluenesulfonic acid; DPPA: diphenylphosphorylazide; DMSO: dimethylsulfoxide; Pd/C Palladium on carbon; Boc: tert-butoxycarbonyl; CBz: benzyloxycarbonyl; DCC 1,3-dicyclohexylcarbodiimide; IR: Infrared; NMR: Nuclear Magnetic Resonance; MS: Mass Spectrum; PES: Positive mode electrospray; sh.: shoulder; S: strong; s: singlet; d: doublet; t: triplet; quad: quadruplet; quint: quintuplet; b: broad; m: multiplet; J: coupling constant; Rf: retention factor (chromatography); Cq: quaternary carbon.

The NMR spectral data provided in the following examples were interpreted based on the identification of the hydrogen atoms of the aromatic moieties as follows:

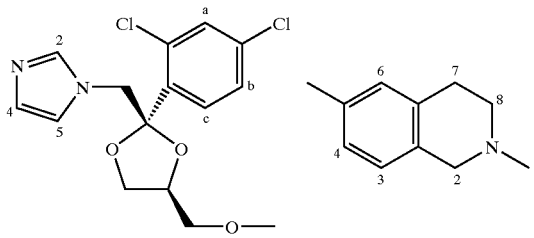

Preparation 1 a) Substitution (Introduction of the Imidazole):

1-(2,4-dichlorophenyl)-2-(1H-imidazol-1-yl)-ethanone

Trichlorinated derivative, 2-chloro-1-(2,4-dichlorophenyl)-ethanone (5.58 g), is added to 5.10 g of imidazole (75 mmole) in 25 ml of acetonitrile, and the reaction medium is stirred at ambient temperature for 24 hours. Then 50 ml of dichloromethane and 50 ml of water are added, followed by extracting, decanting, washing then re-extracting with dichloromethane. The organic phases are dried and evaporated under reduced pressure until a dry extract is obtained, which is purified by chromatography on silica eluting with a $CH_2Cl_2$/MeOH mixture 96/4 to afford 4.76 g of the expected product.

NMR ($CDCl_3$, 300 MHz, δ, ppm): 5.35 (s, 2H, N—$CH_2$—CO); 6.95 (s) and 7.13 (s) 2H H4 and H5; 7.38 (dd, 1H, Hb); 7.51 (d, 1H, Ha); 7.56 (bs, 1H, H2); 7.58 (d, 1H, Hc)

b) Formation of the Epoxide:

1-[[2(2,4-dichlorophenyl)oxiranyl]methyl]-1H-imidazole (P1)

Sodium hydride (0.317 g, 6.6 mmole) and 1.53 g of imidazole derivative (6 mmole) are added to 1.32 g of trimethylsulfoxonium iodide (6 mmole) in 15 ml of DMF, and the reaction medium is stirred for 5 hours at 70° C.–75° C. The reaction medium is then poured into water, extracted with ether, dried then evaporated under reduced pressure in order to obtain the crude product in the form of an oil which is purified by chromatography eluting with a $CH_2Cl_2$/MeOH mixture 95/5 to afford 0.853 g of the title compound. NMR ($CDCl_3$, 300 MHz, δ, ppm): 2.86 and 2.95 (AB, 2H, O—$CH_2$—Cq); 4.12 and 4.66 (AB, 2H, N—$CH_2$—Cq); 6.89 (bs) and 7.02 (bs) 2H H4 and H5; 7.09 (d, 1H, Hc); 7.16 (dd, 1H, Hb); 7.39 (bs, 1H, H2); 7.41(d, 1H, Ha).

Preparation 2 a) Substitution (Introduction of the Imidazole):

1-(2,4-difluorophenyl)-2-(1H-1,2,4-imidazol-1-yl)-ethanone 2-chloro-1-(2,4-difluorophenyl)-ethanone (0.572 g) is added to 0.612 g of imidazole (9 mmole) in 3 ml of acetonitrile and the reaction medium is stirred at ambient temperature for 24 hours. Extraction is then carried out with dichloromethane, followed by washing, drying and evaporation under reduced pressure until the crude product is obtained in the form of oil which is recrystallized from ether to afford 0.521 g of expected product; M.p.=121° C. NMR ($CDCl_3$, 300 MHz, δ, ppm): 5.32 (m, 2H, CO—$CH_2$—N); 6.94 (bs) and 7.15 (bs): 2H H4 and H5; 6.98 (ddd, 1H, Ha); 7.08 (ddd, 1H, Hb); 7.56 (bs, 1H, H2); 8.05 (dt, 1H, Hc)

b) Formation of the Epoxide:

1-[[2-(2,4-difluorophenyl)oxiranyl]methyl]-1H-1,2,4-imidazole (P2)

50% NaH (0.211 g, 44 mmole) is added to 0.88 g (4 mmole) of trimethylsulfoxonium iodide in DMSO (10 ml), the reaction medium is stirred for 30 minutes, then 0.889 g (4 mmole) of imidazole derivative prepared in the previous stage is added by portions and heating is carried out for 3 hours at 60° C. 20 ml of water is added, followed by extracting with ether, drying over $Na_2SO_4$, filtration and evaporation under reduced pressure in order to obtain the crude product (1.16 g) in the form of an oil which is purified by chromatography eluting with a dichloromethane/methanol mixture 97/3 to yield 0.52 g of expected product (Rf=0.3. dichloromethane/methanol 97/3).

NMR ($CDCl_3$, 300 MHz, d, ppm): 2.85 and 2.94 (AB, 2H, $OCH_2$—); 4.11 and 4.62 (AB, 2H, N—$CH_2$); 6.90 (s) 6.99 (s) H4 and H5; 7.38 (s) H2; 6.81 (m, 2H) 7.14 (m, 1H): Ha, Hb, Hc.

Preparation 3

Formation of the Epoxide:

1-[[2(2,4-difluorophenyl)oxiranyl]methyl]-1H-1,2,4-triazole (P3)

A mixture consisting of 2.23 g of triazole derivative (1-(2,4-difluorophenyl)-2-(1H-1,2,4-triazol-1-yl) ethanone) (Commercial: D and O Pharmachem), 15 ml of 5N sodium bicarbonate, 2.2 g of trimethylsulfonium iodide (10 mmole) and 0.088 g of cetrimide (Jansen) in 15 ml of DMF is stirred for 3 hours at 70° C. The reaction medium is then evaporated under reduced pressure in order to obtain the crude product in the form of an oil which is purified by chromatography eluting with an ethyl acetate/methanol mixture 7/3 to afford 0.689 g of expected product.

NMR ($CDCl_3$, 300 MHz, δ, ppm): 2.90 and 2.97 (AB, 2H, O—$CH_2$—Cq); 4.53 and 4.86 (AB, 2H, Cq—$CH_2$—N); 7.19 (td, 1H, Hc); 6.83 (m, 2H, Ha and Hb); 7.91 (s) and 8.20 (s, 2H, N=CH—N).

Preparation 4

4-hydroxy-N-methyl-N-(3-phenyl-2(E)-propenyl)-benzene-methanamine (P4)

Stage a): 4-methoxy-N-methyl-N-(3-phenyl-2(E)-propenyl)-benzenemethanamine

A solution containing trans-cinnamaldehyde (Jansen, d=1.048, 13.2 g, 0.1 mol) and 4-methoxybenzylamine (Fluka, d=1.057, 13.7 g, 0.1 mol) in 250 ml of toluene is heated to reflux for 2 hours 30 minutes, whilst eliminating the water formed during the reaction using a "Dean-Stark" apparatus, then the toluene is evaporated off under reduced pressure. The residue obtained (Schiff base) is then dissolved in 150 ml of methanol then the Schiff base is reduced by adding 3.8 g of $NaBH_4$ at 40° C. 81 ml of 37% formaldehyde is finally added to the reaction medium (amino reduction reaction), the mixture is refluxed for 30 minutes and stirred overnight at ambient temperature. After evaporation of the methanol, the residue is taken up in dichloromethane, washed twice with water and once with brine (saturated aqueous solution of NaCl), dried over MgSO$_4$, filtered and evaporated under reduced pressure until a dry extract is obtained which is repurified by chromatography on silica eluting with a CH$_2$Cl$_2$/AcOEt mixture 70/30 to yield 9.07 g of crystallized expected product. Rf 0.20 CH$_2$Cl$_2$/AcOEt 70/30.

NMR $^1$H (300 MHz, CDCl$_3$, δ, ppm): 2.23 (s, 3H, CH$_3$—N); 3.18 (bd, 2H, N—CH$_2$—CH=CH—Ph); 6.31 (td, J=16; 6.5 Hz, N—CH$_2$—CH=CH—Ph); 6.54 (d, 1H, J=16 Hz, N—CH$_2$—CH=CH—Ph); 3.49 (s, 2H, Ph—CH$_2$—N); 3.80 (s, 3H, Ph—O—CH$_3$); 6.86 and 7, 25 AA'BB'; 7.31 (bt, 2H, H meta); 7.38 (bd, 2H, H ortho); 7.24 (masked 1H, H para).

Stage b): 4-hydroxy-N-methyl-N-(3-phenyl-2(E)-propenyl)-benzenemethanamine

48% hydrobromic acid (20 ml) is added to a solution of product prepared in the previous stage (1 g, 3.74 mmol) in 20 ml of acetic acid, and the reaction medium is heated to reflux for 5 hours and 30 minutes. After evaporation under reduced pressure, entraining the water with ethyl acetate, a dry extract is obtained which is purified by chromatography on silica eluting with a CH$_2$Cl$_2$/MeOH mixture 95/5 in order to obtain 660 mg of expected product. Rf 0.46 CH$_2$Cl$_2$/MeOH 95/5.

Example 1 alpha-[[[2-[3-(4-chlorophenyl)-2(E)-propenyl]-1,2,3,4-tetrahydro-6-isoquinolinyl]oxy]methyl]-alpha-(2,4-dichlorophenyl)-1H-imidazol-1-ethanol

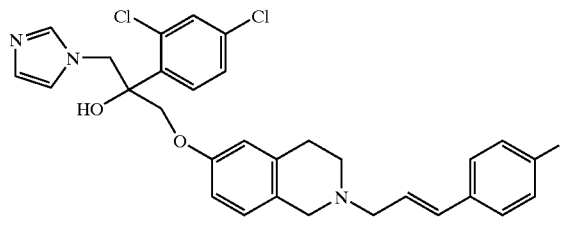

A mixture containing (P1) (0.17 g), (2-[3-(4-chlorophenyl)-2(E)-propenyl]-1,2,3,4-tetrahydro-6-isoquinolinol) (0.18 g) (prepared according to WO 00/20413), 18-C-6 (17 mg) and K$_2$CO$_3$ (0.341 g) in 2 ml of DMF is stirred for 32 hours at 80° C. then extracted with dichloromethane, washed with water, dried over MgSO$_4$, filtered and evaporated under reduced pressure in order to obtain 0.612 g of crude product which is purified by chromatography on silica eluting with a CH$_2$Cl$_2$/MeOH/NH$_4$OH mixture 95/5/0.3 then with acetone/heptane 1/1 then once again with CH$_2$Cl$_2$/MeOH/NH$_4$OH 95/5/0.3 in order to obtain 0.1 g of expected product, Rf=0.28.

$^1$H NMR (CDCl$_3$, 300 MHz, δ, ppm): 2.66 (m, 2H CH$_2$ in position 7); 2.77 (m, 2H, CH2 in position 8); 3.25 (bd, 2H N—CH$_2$—CH=CH—Ph); 6.39 (td, 1H J=16, 7 Hz); 6.60 (bd, 1H); 4.50 4.77 (AB) and 4.27 4.48 (AB): 4H, N—CH$_2$—Cq—CH$_2$—O; 7.37 (masked, Hb); 6.67 (m, 2H, H6 and H4); 6.94 (d, H3); 7.65 (d, 1H, Hc); 7.56 (d, 1H, Ha); 7.38 7.50 AA'BB' 4H aromatic H; 6.34 (s, 1H, OH); 6.70 (bs) 7.37 (bs) and 6.87 (bs) 3H H2', H4' and H5'; 3.50 (bs, 2H, CH$_2$ in position 2). IR (CDCl$_3$): 3563 cm$^{-1}$ (—OH); 1610 cm$^{-1}$ (C=C); 1590, 1556, 1505 and 1491 cm$^{-1}$ (heterocycle+aromatic).

Example 2 alpha-(2,4-dichlorophenyl)-alpha-[[4-[[[methyl(3-phenyl-2(E)-propenyl)]amino]methyl]phenoxy]methyl]-1H-imidazol-1-ethanol

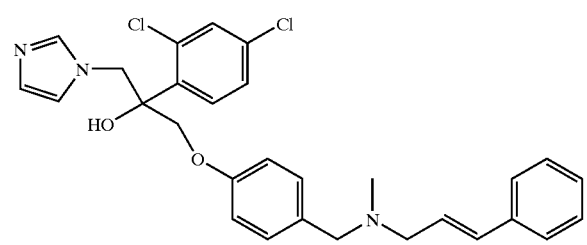

A mixture consisting of (P1) (0.152 g, 0.6 mmole), 4-hydroxy-N-methyl-N-(3-phenyl-2(E)-propenyl)-benzenemethanamine (P4)(0.24 g, 0.9 mmole), 18-C-6 (17 mg) and K$_2$CO$_3$ (0.124 g, 0.9 mmole) in 2 ml of DMF is stirred for 5 hours at 80° C. then extracted with dichloromethane, washed with water, dried over Na$_2$SO4, filtered and evaporated under reduced pressure in order to obtain 0.5 g of crude product which is purified by chromatography on silica eluting with the CH$_2$Cl$_2$/MeOH/NH$_4$OH mixture 95/5/0.3 in order to obtain 71 mg of expected pure product (purity=95%). Rf=0.2 (CH$_2$Cl$_2$/MeOH/NH$_4$OH 95/5/0.3)

$^1$H NMR (CDCl$_3$, 300 MHz, δ, ppm): 2.10 (s, N—CH$_3$); 3.11 (d, N—CH$_2$—CH=CH); 6.32 (dt, J=16 and 7 Hz, N—CH$_2$—CH=CH); 6.54 (d, J=16 Hz, N—CH$_2$—CH=CH); 3.43 (s, Ph—CH$_2$—N); 4.31 (d, J=10) 4.51 (d, J=10): AB =C—N—CH$_2$—Cq; 4.52 (d, J=14.5) 4.79 (d, J=14.5): AB Ph —O—CH$_2$—Cq; 6.86 and 7.22 (AA'BB') O—Ph; 6.35 (s, 1H assumed mobile); 6.70 (s) 6.88 (s) 7.38 (s) 3H imidazole; 7.56 (d, H2); 7.20 to 7.47 (m) H of the phenyl; 7.37 (masked, H6); 7.66 (d, H5).

Example 3 alpha-[[[2-[3-(4-chlorophenyl)-2(E)-propenyl]-1,2,3,4-tetrahydro-6-isoquinolinyl]oxy]methyl]-alpha-(2,4-difluorophenyl)-1H-1,2,4-triazol-1-ethanol

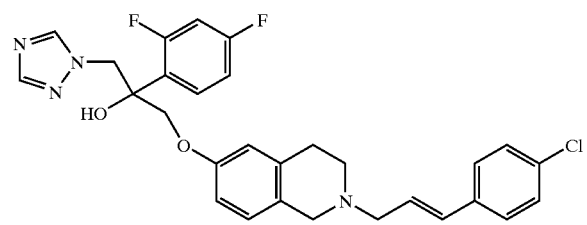

A mixture containing (P3) (0.2 g, 0.66 mmole), (2-[3-(4-chlorophenyl)-2(E)-propenyl]-1,2,3,4-tetrahydro-6- isoquinolinol) (prepared according to WO 00/20413) (0.144 g, 0.6 mmole), 18-C-6 (15 mg) and K₂CO₃ (0.167 g, 1.2 mmole) in 2 ml of DMF is stirred for 2 hours at 80° C. then extracted with dichloromethane, washed with water, dried over Na₂SO₄, filtered and evaporated under reduced pressure in order to obtain 0.49 g of crude product which is purified by chromatography on silica eluting with a CH₂Cl₂/MeOH/NH₄OH mixture 94/6/0.3 in order to obtain 0.2 g of expected pure product. Rf=0.35 (CH₂Cl₂/MeOH/NH₄OH 95/5/0.3).

¹H NMR (CDCl₃, 300 MHz, δ, ppm): 2.82 (m, 2H CH₂ in position 7); 2.88 (m, 2H, CH2 in position 8); 3.66 (bs, =C—C$\underline{H}_2$—N; 3.37 (bd, 2H N—C$\underline{H}_2$—CH=CH—Ph); 6.34 (dt, 1H J=16, 7 Hz, N—CH₂—C$\underline{H}$=CH—Ph); 6.55 (dt, 1H J=16 Hz, N—CH₂—CH=C$\underline{H}$—Ph); 4.20 (AB, C—CH2—O); 4.85 (AB, N—CH₂—C); 6.62 (d, H'a); 6.66 (dd, H'c); 6.93 (d, H'b); 6.82 (m, Ha and Hb); 7.460 (dt, Hc); 7.83 (s) and 8.02 (s): H3 and H5 IR (CDCl₃): 3565 cm⁻¹ (—OH); 1670, 1618, 1501 and 1491 cm⁻¹ (—C=C—, heterocycle+aromatics).

Example 4 alpha-(2,4-difluorophenyl)-alpha-[[4-[[methyl(3-phenyl-2(E)-propenyl)amino]methyl]phenoxy] methyl]-1H-1,2,4-triazol-1-ethanol

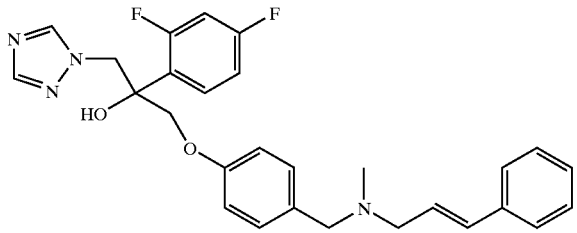

A mixture containing (P3) (0.145 g, 0.61 mmole), 4-hydroxy-N-methyl-N-(3-phenyl-2(E)-propenyl)-benzenemethanamine (P4) (0.152 g, 0.6 mmole), 18-C-6 (11 mg) and K₂CO₃ (0.167 g, 1.2 mmole) in 2 ml of DMF is agitated for 2 hours at 80° C. then extracted with dichloromethane, washed with water, dried over Na₂SO₄, filtered and evaporated under reduced pressure in order to obtain 0.391 g of crude product which is purified by chromatography on silica eluting with a CH₂Cl₂/MeOH/NH₄OH mixture 94/6/0.3 in order to obtain 0.163 mg of expected pure product (purity=95%). Rf=0.25 (CH₂Cl₂/MeOH/NH₄OH 95/5/0.3).

¹H NMR (CDCl₃, 300 MHz, δ, ppm): 2.23 (s, N—CH₃); 3.18 (d, N—C$\underline{H}_2$—CH=CH); 6.29 (td, J=16 and 6.5 Hz, N—CH₂—C$\underline{H}$=CH); 6.53 (bd, J=16 Hz, N—CH₂—CH=C$\underline{H}$); 3.50 (s, Ph—C$\underline{H}_2$—N); 4.21 4.26 (AB, 2H) and 4.83 4.90 (AB, 2H): =C—N—C$\underline{H}_2$—Cq and Ph —O—C $\underline{H}_2$—Cq; 4.47 (1H, OH); 6.84 and 7.24 (AA'BB') O—Ph; 6.85 (m, 2H) 7.61 (td 1H) 3H imidazole Ha, Hb and Hc; 7.84 (s) and 8.03 (s) 2H H2 and H4; 7.20 to 7.40 (m) H of the phenyl.

Example 5 alpha-(2,4-difluorophenyl)-alpha-[[4-[[(2-amino-ethyl)[3-(4-chlorophenyl)-2(E)-propenyl]-amino]-methyl]-phenoxy]-methyl]-1H-imidazol-1-ethanol

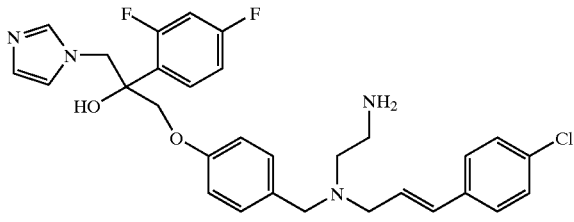

Stage a): Opening of the Epoxide

4-[2-(2,4-difluorophenyl)-2-hydroxy-3-(1H-imidazol-1-yl)-propoxy]benzaldehyde

A mixture containing 1-[[2-(2,4-difluorophenyl)-oxiranyl]-methyl]-1H-imidazole (P2) (0.5 g, 2.1 mmole), 4-hydroxy-benzaldehyde (0.31 g, 2.5 mmole) K₂CO₃ (0.41 g, 2.9 mmole), 18-C-6 (25 mg) in 5 ml of DMF is stirred for 6 hours, extracted with dichloromethane, washed with 2N sodium bicarbonate, dried over Na₂SO₄, filtered and evaporated under reduced pressure in order to obtain 0.957 g of crude product which is purified by chromatography eluting with a CH₂Cl₂/MeOH mixture 97/3 in order to obtain 0.557 mg of expected product. Rf=0.12 (CH₂Cl₂/MeOH 97/3).

¹H NMR (DMSO, 300 MHz, δ, ppm): 4.27 4.40 AB 2H and 4.48 (bs, 2H): N—CH₂—Cq and 0—CH₂—Cq; 6.37 (bs, 1H, OH); 6.73 (bs) and 6.91 (bs) 2H H4 and H5; 7.39 (bs, 1H, H2); 7.11 and 7.85 AA'BB' 4H —O—Ph); 7.53 (td, 1H, Hc); 7.21 (ddd, 1H, Ha); 7.04 (td, 1H, Hb); 9.86 (s, 1H, CHO).

Stage b) Amino-Reduction 1,1-dimethylethyl [2-[[[4-[2-(2,4-difluorophenyl)-2-hydroxy-3-(1H-imidazol-1-yl)propoxy]phenyl] methyl]amino]ethyl]-carbamate A mixture containing the product prepared in Stage a (0.55 g, 1.5 mmole), the mono BOC protected diamine, 1,1-dimethylethyl 2-aminoethyl-carbamate (0.27 g, 1.68 mmole), acetic acid (0.128 ml) in 5.5 ml of methanol is stirred for 2 hours at ambient temperature, then NaBH₃CN (0.125 g, 1.98 mmole) is added. The reaction medium is stirred for a further 2 hours at ambient temperature, taken up in dichloromethane, dried over MgSO₄, filtered then evaporated under reduced pressure in order to obtain 0.678 g of crude product which is purified by chromatography eluting with a CH₂Cl₂/MeOH/NH₄OH mixture 95/5/0.3 to afford 0.425 g of expected pure product. Rf=0.18 CH₂Cl₂/MeOH/NH₄OH 95/5/0.3.

¹H NMR (DMSO, 300 MHz, δ, ppm): 1.43 (s, 9H, OC(CH₃)₃; 2.76 (m, 2H HN—C$\underline{H}_2$—CH₂—NH); 3.23 (m, 2H, HN—CH₂—C$\underline{H}_2$—NH); 5.13 (bs, 1H, HN—CH₂—CH₂—N$\underline{H}$); 3.76 (bs, 2H, NH—CH₂—Ph); 4.23 4.27 AB and 4.45 4.52 AB: N—CH₂—Cq and 0—CH₂—Cq; 6.82 and 7.26 AA'BB' 4H —O—Ph); 6.80 (bs) and 6.88 (bs) 2H H4 and H5; 7.38 (bs, H2); 6.85 (m, 2H, Hb and Ha); 7.56 (td, 1H, Hc)

Stage c) Amino Reduction 1,1-dimethyl-ethyl 2-[3-(4-chlorophenyl)-2(E)-propenyl]-[[[4-[2-(2,4-difluorophenyl)-2-hydroxy-3-(1H-imidazol-1-yl)-propoxy]-phenyl]-methyl]-amino]-ethyl]-carbamate A mixture containing the product prepared in Stage b (0.4 g, 0.79 mmole), aldehyde (0.146 g, 0.84 mmole), acetic acid (68 µl) in 5 ml of methanol is stirred for 2 hours at ambient temperature then NaBH$_3$CN (0.065 g, 1 mmole) is added. The reaction medium is stirred overnight at ambient temperature, water is added, the pH is adjusted with concentrated NH$_4$OH, followed by extraction with dichloromethane, drying over MgSO$_4$, filtration then evaporation under reduced pressure in order to obtain 0.507 g of crude product which is purified by chromatography eluting with a CH$_2$Cl$_2$/MeOH/NH$_4$OH mixture 95/5/0.3 to afford 0.36 g of expected pure product. Rf=0.2 CH$_2$Cl$_2$/MeOH/NH$_4$OH 95/5/0.3.

Stage d) Deprotection alpha-(2,4-difluorophenyl)-alpha-[[4-[[(2-aminoethyl)[3-(4-chlorophenyl)-2(E)-propenyl]amino]methyl]phenoxy]methyl]-1H-imidazol-1-ethanol Trifluoroacetic acid (3.3 ml) is added to 0.33 g of product obtained in Stage c in 5 ml of dichloromethane, whilst cooling down by an ice bath, the reaction medium is stirred for 30 minutes at 0–5° C., then left to return to ambient temperature and stirred for a further period of 3 hours. After evaporation under reduced pressure, a mixture of dichloromethane and water is added to the dry extract, the pH is adjusted to 8 with concentrated NH$_4$OH, followed by extraction with dichloromethane, the organic phases are dried with MgSO$_4$, filtered and evaporated under reduced pressure in order to obtain 0.284 g of crude product which is purified by chromatography eluting with a CH$_2$Cl$_2$/MeOH/NH$_4$OH mixture 90/10/0.3 to yield 0.121 g of expected pure product. Rf=0.25 CH$_2$Cl$_2$/MeOH/NH$_4$OH 90/10/0.3.

$^1$H NMR (CDCl$_3$, 300 MHz, δ, ppm): 2.59 (N—CH$_2$—CH$_2$—NH$_2$); 2.76 (N—CH$_2$—CH$_2$—NH$_2$); 3.25 (N—CH$_2$—CH=CH); 6.23 (N—CH$_2$—CH=CH); 6.46 (N—CH$_2$—CH=CH); 3.56 (Ph—CH$_2$—N); 4.44 4.54 (AB, 2H) and 4.20 4.27 (AB, 2H): =C—N—CH$_2$—Cq and Ph—O—CH$_2$—Cq; 6.80, 7.14 to 7.24 O—Ph; 6.80 (2H) 7.38 (1H) 3H imidazole Ha, Hb and Hc; 6.84 and 7.56 H2 and H4; 7.25 to 7.29 H of the phenyl.

Pharmaceutical Compositions

| Compositions were prepared containing | |
| --- | --- |
| Product of Example 1 | 50 mg |
| Excipient q.s.f. | 1 g |
| Detail of the excipient: starch, talc, magnesium stearate. | |

Biological Activity

1) Antifungal Activity of the Compounds According to the Invention.

Female mice weighing from 18 to 22 g were used. A quantity of *Candida albicans* 44858 was administered into the tail vein at a rate of 10$^6$ CFU per mouse (CFU: colony forming unit). The mice are separated into 5 groups of 5 mice and treated as follows:

One Hour after the Infection
  Group 1: the mice are treated with the product P 25 mg/kg by oral route
  Group 2: the mice are treated with the product P by intraperitoneal route at a rate of 25 mg/kg
  Group 3: the mice are treated with fluconazole (25 mg/kg by oral route).
  Group 4: the mice are treated with fluconazole (25 mg/kg by intraperitoneal route).
  Group 5: the mice receive no antifungal treatment.
Over a period of 22 days, the dead mice are counted.

2) Minimum Inhibitory Concentration (MIC)

*Candida albicans* cells are prepared as indicated in Journal of Antimicrobial Chemotherapy 38, 579–587, washed 3 times with a 0.1 M phosphate solution and used immediately in order to determine the minimum inhibitory concentration (MIC).

The MICs are determined by the modification of a microtiter plate according to the standard method of the Comité National des standards cliniques de laboratoire. RPMI-1640 is used as medium, and L-glutamine buffered to pH 7 with a 0.15 M MOPS (3-[N-morpholino]propane sulfonic acid) solution. *Candida albicans* cells (1.5×10$^3$ cells/ml) are added to the wells of a 96-well plate containing RPMI-1640 and the dilutions of antifungal agents. The results were read 48 hours after incubation at 35° C. and the MIC or minimum inhibitory concentration which inhibits the growth of *Candida albicans* cells was determined.

3) Minimum Fungicidal Concentration

After the MIC reading at 48 hours, the plates are shaken and 10 µL of aliquot is removed from the wells, and placed on rectangular disks containing dextrose agar. The plates are incubated for 48 hours at 35° C. The minimum fungicidal concentration is the concentration of the antifungal agent at which the number of colony forming units is zero.

Conclusion

The compounds according to the invention described in Examples 1 to 5 show an activity of <100 µg/ml in the MIC test.

What is claimed is:
1. A compound of formula (I)

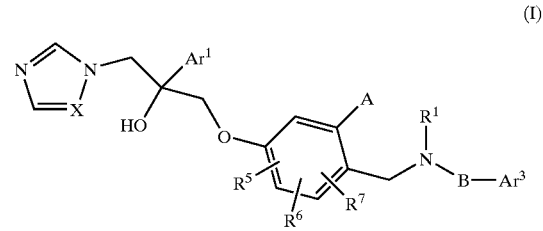

wherein
  X is nitrogen or CH;
  Ar$^1$ is a carbocyclic or heterocyclic aryl, non-substituted or substituted by one or more R$^2$, R$^3$ or R$^4$;
  A is hydrogen or CH$_2$ bonding with R$^1$ forms a fused six membered ring with the phenyl;
  Ar$^3$ is a carbocyclic or heterocyclic aryl, non-substituted or substituted by one or more R$^8$, R$^9$ or R$^{10}$;

B is $(C_1-C_4)$-alkylene-CH=CH— or $(C_1-C_4)$-alkylene-cyclopropylene, said cyclopropylene or —CH=CH— being non-substituted or substituted by $R^2$ or $R^3$;

$R^1$ is hydrogen, —SO$_3$H, $(C_1-C_6)$-alkyl, non-substituted or substituted by $R^2$, or is CH$_2$ bonding with A forms a fused six membered ring with the phenyl;

$R^2$, $R^3$, $R^4$, $R^5$, $R^6$, $R^7$, $R^8$, $R^9$ or $R^{10}$ are the same or different and are independently selected from the group consisting of: fluorine, chlorine, bromine, cyano, mono- bi- or trihalogeno$(C_1-C_8)$alkyl, mono- bi- or trihalogeno$(C_1-C_8)$-alkyloxy, hydroxy, nitro, carboxyl, formyl, —SO$_3$H, —OSO$_3$H, $(R^{11}O)_2P(O)$—, $(R^{11}O)_2P(O)$—O—, amino, $(C_1-C_8)$-alkylamino, di$((C_1-C_8)$alkyl)amino, $(C_5-C_{14})$-aryl-$(C_1-C_6)$-alkylenamino or $(C_5-C_{14})$-arylamino, $(C_1-C_8)$-alkyl, $(C_5-C_{14})$-aryl, a heterocycle optionally substituted by oxo, $(C_5-C_{14})$-aryl-$(C_1-C_6)$alkyl, amino-$(C_1-C_6)$-alkyl, $(C_1-C_8)$-alkylamino-$(C_1-C_6)$-alkyl, di-$((C_1-C_8)$alkyl)amino-$(C_1-C_6)$-alkyl, hydroxy-$(C_1-C_6)$alkyl, $(C_1-C_6)$-alkyloxy-$(C_1-C_6)$-alkyl, $(C_1-C_8)$-alkyloxy optionally interrupted by one or more oxygen atoms, $(C_5-C_{14})$-aryl-$(C_1-C_6)$-alkylenoxy, $(C_5-C_{14})$-aryloxy, hydroxy-$(C_1-C_6)$alkylenoxy, $(C_1-C_6)$-alkyloxy-$(C_1-C_6)$-alkylenoxy, amino-$(C_1-C_6)$-alkylenoxy, $(C_1-C_6)$-alkylamino-$(C_1-C_6)$-alkylenoxy, di$((C_1-C_8)$-alkyl)amino-$(C_1-C_6)$-alkylenoxy, methylenedioxy, $(C_1-C_6)$-alkyloxycarbonyl, $(C_1-C_6)$-alkylcarbonyl, $(C_5-C_{14})$aryl-$(C_1-C_6)$-alkylenecarbonyl, $(C_5-C_{14})$-arylcarbonyl, $(C_1-C_6)$-alkylaminocarbonyl, $(C_1-C_6)$-alkanoylamino, $(C_1-C_6)$-alkylsulfonylamino, $(C_5-C_{14})$-aryl-sulfonylamino, $(C_5-C_{14})$-aryl-$(C_1-C_6)$-alkylenesulfonylamino, $(C_1-C_6)$-alkylaminosulfonyl, $(C_5-C_{14})$-aryl-$(C_1-C_6)$-alkylenaminosulfonyl, $(C_1-C_6)$-alkylsulfonyl, $(C_5-C_{14})$-aryl-$(C_1-C_8)$-alkylenesulfonyl or $(C_5-C_{14})$-aryl-sulfonyl, said alkyl, aryl or heterocycles are optionally substituted; and wherein $R^{11}$ is hydrogen, $(C_1-C_{10})$-alkyl, $(C_6-C_{14})$-aryl or $(C_6-C_{14})$-aryl-$(C_1-C_6)$-alkyl, or an enantiomer, a stereoisomer, a tautomer or a mixture thereof, or a physiologically acceptable salt, a solvate or a derivative thereof, or a prodrug thereof.

2. The compound of formula (I) according to claim 1, wherein B is —CH$_2$—CH=CH— or —CH$_2$-(cyclopropyl)-, said groups being non-substituted or substituted by one or more halogens or $(C_1-C_4)$-alkyl; Ar$^1$ is phenyl, or a physiologically acceptable salt thereof.

3. The compound of formula (I) according to claim 1 having the formula (IA):

(IA)

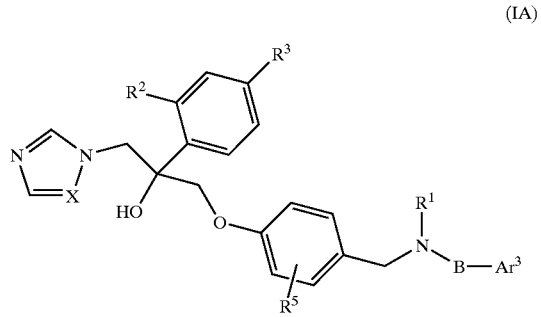

wherein, B, X, Ar$^3$, R$^5$ and R$^1$ are as defined in claim 1, R$^2$ and R$^3$ are halogen, or a physiologically acceptable salt thereof.

4. The compound of formula (I) according to claim 1 having the formula (IB):

(IB)

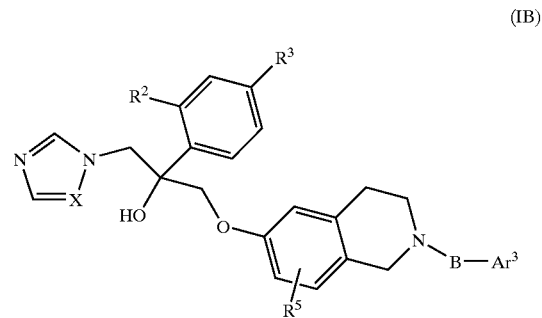

wherein B, X, Ar$^3$ and R$^5$ are as defined in claim 1, R$^2$ and R$^3$ are halogen, or a physiologically acceptable addition salt thereof.

5. The compound of formula (I) according to claim 1, wherein R$_2$ and R$_3$ are fluorine or chlorine, X is CH or N and Ar$^3$ is phenyl, non-substituted or substituted by R$^8$ as defined in claim 1, or a physiologically acceptable addition salt thereof.

6. The compound of formula (I) according to claim 1, wherein R$^1$ is hydrogen or, methyl or ethyl, non-substituted or substituted by F, OH, NH$_2$, $(C_1-C_6)$-alkyloxy, $(C_1-C_6)$-alkylamino, pyrrolidino, 2-oxopyrrolidino or di-$(C_1-C_6)$-alkylamino group, or a physiologically acceptable addition salt thereof.

7. The compound of formula (I) according to claim 1, wherein Ar$^3$ is phenyl, non-substituted or substituted by R$^8$, representing —Cl, —F, CN, —CF$_3$, —OCF$_3$, —OH, —NH$_2$, $(C_1-C_6)$-alkyloxy, $(C_1-C_6)$-alkylamino, or di-$(C_1-C_6)$-alkylamino or a heterocycle chosen from:

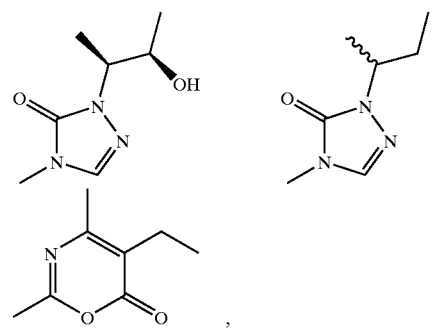

or a physiologically acceptable addition salt thereof.

8. The compound of formula (I) according to claim 1 selected from the group consisting of:
alpha-[[[2-[3-(4-chlorophenyl)-2(E)-propenyl]-1,2,3,4-tetrahydro-6-isoquinolinyl]oxy]methyl]-alpha-(2,4-dichlorophenyl)-1H-imidazol-1-ethanol;
alpha-(2,4-dichlorophenyl)-alpha-[[4-[[[methyl(3-phenyl-2(E)-propenyl)]amino]methyl]phenoxy]methyl]-1H-imidazol-1-ethanol;
alpha-(2,4-difluorophenyl)-alpha-[[4-[[methyl(3-phenyl-2(E)-propenyl)amino]methyl]phenoxy]methyl]-1H-1,2,4-triazol-1-ethanol;
alpha-[[[2-[3-(4-chlorophenyl)-2(E)-propenyl]-1,2,3,4-tetrahydro-6-isoquinolinyl]oxy]methyl]-alpha-(2,4-difluorophenyl)-1H-1,2,4-triazol-1-ethanol; and alpha-(2,4-difluorophenyl)-alpha-[[4-[[(2-aminoethyl)[3-(4-chlorophenyl)-2(E)-propenyl]amino]methyl]phenoxy]methyl]-1H-imidazol-1-ethanol.

9. A process for the preparation of a compound of formula (IA) according to claim 3 comprising: reacting a compound of formula (II)

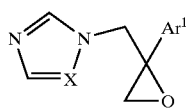
(II)

wherein X and Ar$^1$ are as defined in claim 3, with a compound of formula (IIIa):

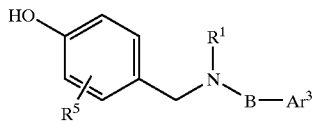
(IIIa)

wherein R$^1$, B, R$^5$ and Ar$^3$ are as defined in claim 3, in a basic medium, to obtain the corresponding compound of formula (IA) as defined in claim 3.

10. A process for the preparation of a compound of formula (IB) according to claim 4 comprising: reacting a compound of formula (II)

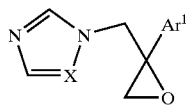
(II)

wherein X and Ar$^1$ are as defined in claim 4, with a compound of formula (IIIa) or (IIIb)

(IIIb)

wherein B, R$^5$ and Ar$^3$ are as defined in claim 4, in a basic medium, to obtain the corresponding compound of formula (IB) as defined in claim 4.

11. A process for the preparation of a compound of formula (I) according to claim 1 comprising: reacting a compound of formula (II):

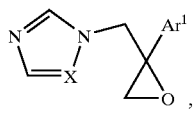
(II)

with a compound of formula (III'), HO—C$_6$H$_4$—CHO, in the presence of a base, the phenyl being non-substituted or substituted by R$^5$ to obtain a compound of formula (IIA):

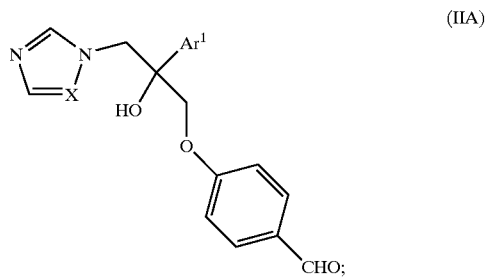
(IIA)

reacting compound of formula (IIA) with an amine of formula, R$^1$—NH$_2$, R$^1$ being as defined in claim 1, the reactive functions of which are optionally protected, followed by a reduction reaction in the presence of a reducing agent chosen from NaBH$_3$CN or BH$_3$.pyridine, to obtain a compound of formula (IIB)

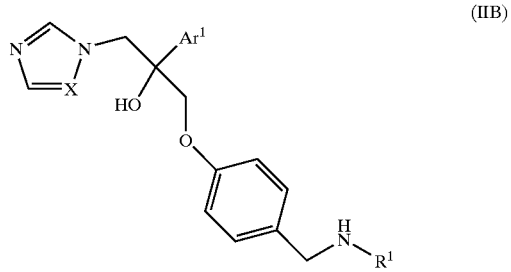
(IIB)

reacting compound of formula (IIB)

either with a compound of formula

OHC—CH=CH—C$_6$H$_4$—R$^8$ or OHC-(Cyclopropyl)-C$_6$H$_4$—R$^8$ followed by a reduction reaction in the presence of a reducing agent chosen from NaBH$_3$CN or BH$_3$.pyridine or with a compound of formula:

AcO—CH$_2$—CH=CH—C$_6$H$_4$—R$^8$ in the presence of a palladium compound to obtain the following compounds of formula (IAA) or (IAB):

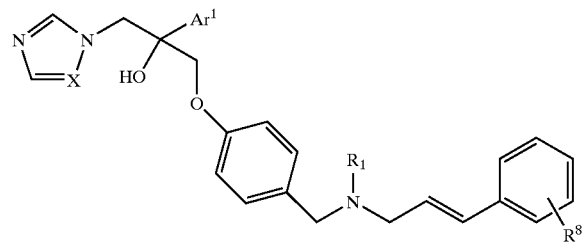
(IAA)

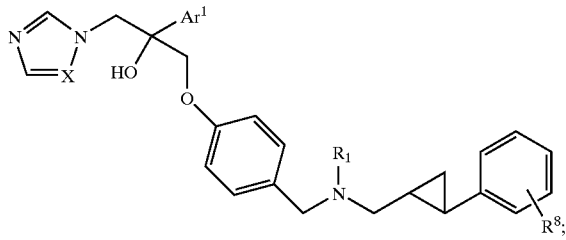

(IAB)

wherein X, Ar¹, R¹, and R⁸ are as defined in claim 1.

12. A method for the treatment of a fungal disease comprising administering to a patient in need of such treatment a therapeutically effective amount of a compound of the formula (I):

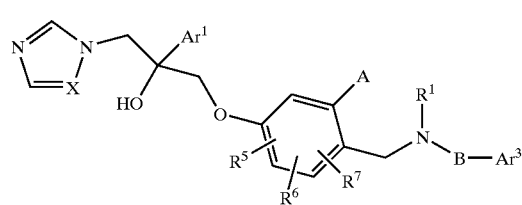

(I)

wherein

X is nitrogen or CH;

Ar¹ is a carbocyclic or heterocyclic aryl, non-substituted or substituted by one or more $R^2, R^3$ or $R^4$;

A is hydrogen or $CH_2$ bonding with $R^1$ forms a fused six membered ring with the phenyl;

Ar³ is a carbocyclic or heterocyclic aryl, non-substituted or substituted by one or more $R^8$, $R^9$ or $R^{10}$;

B is $(C_1-C_4)$-alkylene-CH=CH— or $(C_1-C_4)$-alkylene-cyclopropylene, said cyclopropylene or —CH=CH— being non-substituted or substituted by $R^2$ or $R^3$;

$R^1$ is hydrogen, —$SO_3H$, $(C_1-C_6)$-alkyl, non-substituted or substituted by $R^2$, or is $CH_2$ bonding with A forms a fused six membered ring with the phenyl;

$R^2$, $R^3$, $R^4$, $R^5$, $R^6$, $R^7$, $R^8$, $R^9$ or $R^{10}$ are the same or different and are independently selected from the group consisting of: fluorine, chlorine, bromine, cyano, mono- bi- or trihalogeno$(C_1-C_8)$alkyl, mono- bi- or trihalogeno$(C_1-C_8)$-alkyloxy, hydroxy, nitro, carboxyl, formyl, —$SO_3H$, —$OSO_3H$, $(R^{11}O)_2P(O)$—, $(R^{11}O)_2P$(O)—O—, amino, $(C_1-C_8)$-alkylamino, di$((C_1-C_8)$ alkyl)amino, $(C_5-C_{14})$-aryl-$(C_1-C_6)$-alkylenamino or $(C_5-C_{14})$-arylamino, $(C_1-C_8)$-alkyl, $(C_5-C_{14})$-aryl, a heterocycle optionally substituted by oxo, $(C_5-C_{14})$-aryl-$(C_1-C_6)$alkyl, amino-$(C_1-C_6)$-alkyl, $(C_1-C_8)$-alkylamino-$(C_1-C_6)$-alkyl, di-$((C_1-C_8)$alkyl)amino-$(C_1-C_6)$-alkyl, hydroxy-$(C_1-C_6)$alkyl, $(C_1-C_6)$-alkyloxy-$(C_1-C_6)$-alkyl, $(C_1-C_8)$-alkyloxy optionally interrupted by one or more oxygen atoms, $(C_5-C_{14})$-aryl-$(C_1-C_6)$-alkylenoxy, $(C_5-C_{14})$-aryloxy, hydroxy-$(C_1-C_6)$alkylenoxy, $(C_1-C_6)$-alkyloxy-$(C_1-C_6)$-alkylenoxy, amino-$(C_1-C_6)$-alkylenoxy, $(C_1-C_6)$-alkylamino-$(C_1-C_6)$-alkylenoxy, di$((C_1-C_8)$-alkyl)amino-$(C_1-C_6)$-alkylenoxy, methylenedioxy, $(C_1-C_6)$-alkyloxycarbonyl, $(C_1-C_6)$-alkylcarbonyl, $(C_5-C_{14})$aryl-$(C_1-C_6)$-alkylenecarbonyl, $(C_5-C_{14})$-arylcarbonyl, $(C_1-C_6)$-alkylaminocarbonyl, $(C_1-C_6)$-alkanoylamino, $(C_1-C_6)$-alkylsulfonylamino, $(C_5-C_{14})$-aryl-sulfonylamino, $(C_5-C_{14})$-aryl-$(C_1-C_6)$-alkylenesulfonylamino, $(C_1-C_6)$-alkylaminosulfonyl, $(C_5-C_{14})$-aryl-$(C_1-C_6)$-alkylenaminosulfonyl, $(C_1-C_6)$-alkylsulfonyl, $(C_5-C_{14})$-aryl-$(C_1-C_8)$-alkylenesulfonyl or $(C_5-C_{14})$-aryl-sulfonyl, said alkyl, aryl or heterocycles are optionally substituted; and wherein $R^{11}$ is hydrogen, $(C_1-C_{10})$-alkyl, $(C_6-C_{14})$-aryl or $(C_6-C_{14})$-aryl-$(C_1-C_6)$-alkyl, or an enantiomer, a stereoisomer, a tautomer or a mixture thereof, or a physiologically acceptable salt, a solvate or a derivative thereof, or a prodrug thereof, optionally in combination with a pharmaceutically acceptable carrier.

13. The method according to claim 12 wherein said fungal disease is caused by *Candida albicans, Candida glabrata, krusei, tropicalis, pseudotropicalis, parapsilosis, Aspergillus, Aspergillus flavus, Aspergillus niger, Cryptococcus neoformans, Microsporum canis, Trichophyton rubrun* or *Trichophyton mentagrophyte*.

14. The method according to claim 12 wherein said fungal disease is selected from the group consisting of candidoses, cryptococcoses, bronchopulmonary and pulmonary aspergilloses and invasive aspergilloses in immunodeficient individuals.

15. The method according to claim 14 wherein said candidoses is selected from the group consisting of digestive, urinary, vaginal and cutaneous candidoses.

16. The method as according to claim 14 wherein said cryptococcoses is selected from the group consisting of neuromeningeal, pulmonary and cutaneous cryptococcoses.

17. The method according to claim 12 wherein said compound is selected from the group consisting of:

alpha-[[[2-[3-(4-chlorophenyl)-2(E)-propenyl]-1,2,3,4-tetrahydro-6-isoquinolinyl]oxy]methyl]-alpha-(2,4-dichlorophenyl)-1H-imidazol-1-ethanol;

alpha-(2,4-dichlorophenyl)-alpha-[[4-[[[methyl(3-phenyl-2(E)-propenyl)]amino]methyl]phenoxy]methyl]-1H-imidazol-1-ethanol;

alpha-(2,4-difluorophenyl)-alpha-[[4-[[methyl(3-phenyl-2(E)-propenyl)amino]methyl]phenoxy]methyl]-1H-1,2,4-triazol-1-ethanol;

alpha-[[[2-[3-(4-chlorophenyl)-2(E)-propenyl]-1,2,3,4-tetrahydro-6-isoquinolinyl]oxy]methyl]-alpha-(2,4-difluorophenyl)-1H-1,2,4-triazol-1-ethanol; and alpha-(2,4-difluorophenyl)-alpha-[[4-[[(2-aminoethyl)[3-(4-chlorophenyl)-2(E)-propenyl]amino]methyl]phenoxy]methyl]-1H-imidazol-1-ethanol.

18. A pharmaceutical composition comprising at least one compound of formula (I) according to claim 1 or an enantiomer, a stereoisomer, a tautomer or a mixture thereof, or a physiologically acceptable salt, a solvate or a derivative thereof, or a prodrug thereof in combination with one or more pharmaceutically acceptable carriers.

19. The composition according to claim 18 wherein said compound is selected from the group consisting of:

alpha-[[[2-[3-(4-chlorophenyl)-2(E)-propenyl]-1,2,3,4-tetrahydro-6-isoquinolinyl]oxy]methyl]-alpha-(2,4-dichlorophenyl)-1H-imidazol-1-ethanol;

alpha-(2,4-dichlorophenyl)-alpha-[[4-[[[methyl(3-phenyl-2(E)-propenyl)]amino]methyl]phenoxy]methyl]-1H-imidazol-1-ethanol;

alpha-(2,4-difluorophenyl)-alpha-[[4-[[methyl(3-phenyl-2(E)-propenyl)amino]methyl]phenoxy]methyl]-1H-1,2,4-triazol-1-ethanol;

alpha-[[[2-[3-(4-chlorophenyl)-2(E)-propenyl]-1,2,3,4-tetrahydro-6-isoquinolinyl]oxy]methyl]-alpha-(2,4-difluorophenyl)-1H-1,2,4-triazol-1-ethanol; and alpha-(2,4-difluorophenyl)-alpha-[[4-[[(2-aminoethyl)[3-(4-chlorophenyl)-2(E)-propenyl]amino]methyl]phenoxy]methyl]-1H-imidazol-1-ethanol.

20. A compound of formula:

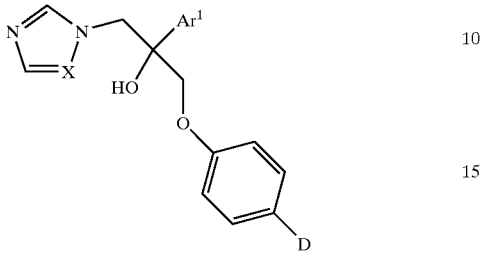

wherein

X is nitrogen or CH;

$Ar^1$ is a carbocyclic or heterocyclic aryl, non-substituted or substituted by one or more $R^2$, $R^3$ or $R^4$;

D is CHO or $CH_2NHR^1$; and wherein $R^1$ is hydrogen, —$SO_3H$, ($C_1$–$C_6$)-alkyl, non-substituted or substituted by $R^2$;

$R^2$, $R^3$ or $R^4$ are the same or different and are independently selected from the group consisting of: fluorine, chlorine, bromine, cyano, mono- bi- or trihalogeno($C_1$–$C_8$)alkyl, mono- bi- or trihalogeno ($C_1$–$C_8$)-alkyloxy, hydroxy, nitro, carboxyl, formyl, —$SO_3H$, —$OSO_3H$, $(R^{11}O)_2P(O)$—, $(R^{11}O)_2P(O)$—O—, amino, ($C_1$–$C_8$)-alkylamino, di(($C_1$–$C_8$)alkyl)amino, ($C_5$–$C_{14}$)-aryl-($C_1$–$C_6$)-alkylenamino or ($C_5$–$C_{14}$)-arylamino, ($C_1$–$C_8$)-alkyl, ($C_5$–$C_{14}$)-aryl, a heterocycle optionally substituted by oxo, ($C_5$–$C_{14}$)-aryl-($C_1$–$C_6$)alkyl, amino-($C_1$–$C_6$)-alkyl, ($C_1$–$C_8$)-alkylamino-($C_1$–$C_6$)-alkyl, di-(($C_1$–$C_8$)alkyl)amino-($C_1$–$C_6$)-alkyl, hydroxy-($C_1$–$C_6$)alkyl, ($C_1$–$C_6$)-alkyloxy-($C_1$–$C_6$)-alkyl, ($C_1$–$C_8$)-alkyloxy optionally interrupted by one or more oxygen atoms, ($C_5$–$C_{14}$)-aryl-($C_1$–$C_6$)-alkylenoxy, ($C_5$–$C_{14}$)-aryloxy, hydroxy-($C_1$–$C_6$)alkylenoxy, ($C_1$–$C_6$)-alkyloxy-($C_1$–$C_6$)-alkylenoxy, amino-($C_1$–$C_6$)-alkylenoxy, ($C_1$–$C_6$)-alkylamino-($C_1$–$C_6$)-alkylenoxy, di(($C_1$–$C_8$)-alkyl)amino-($C_1$–$C_6$)-alkylenoxy, methylenedioxy, ($C_1$–$C_6$)-alkyloxycarbonyl, ($C_1$–$C_6$)-alkylcarbonyl, ($C_5$–$C_{14}$) aryl-($C_1$–$C_6$)-alkylenecarbonyl, ($C_5$–$C_{14}$)-arylcarbonyl, ($C_1$–$C_6$)-alkylaminocarbonyl, ($C_1$–$C_6$)-alkanoylaamino, ($C_1$–$C_6$)-alkylsulfonylamino, ($C_5$–$C_{14}$)-aryl-sulfonylamino, ($C_5$–$C_{14}$)-aryl-($C_1$–$C_6$)-alkylenesulfonylamino, ($C_1$–$C_6$)-alkylaminosulfonyl, ($C_5$–$C_{14}$)-aryl-($C_1$–$C_6$)-alkylenaminosulfonyl, ($C_1$–$C_6$)-alkylsulfonyl, ($C_5$–$C_{14}$)-aryl-($C_1$–$C_8$)-alkylenesulfonyl or ($C_5$–$C_{14}$)-aryl-sulfonyl, said alkyl, aryl or heterocycles are optionally substituted; and wherein $R^{11}$ is hydrogen, ($C_1$–$C_{10}$)-alkyl, ($C_6$–$C_{14}$)-aryl or ($C_6$–$C_{14}$)-aryl-($C_1$–$C_6$)-alkyl, or an enantiomer, a stereoisomer, a tautomer or a mixture thereof, or a physiologically acceptable salt, a solvate or a derivative thereof, or a prodrug thereof.

* * * * *